United States Patent
Angell et al.

(10) Patent No.: US 9,522,927 B2
(45) Date of Patent: *Dec. 20, 2016

(54) DOPO DERIVATIVE FLAME RETARDANTS

(71) Applicant: Albemarle Corporation, Baton Rouge, LA (US)

(72) Inventors: Yu Li Angell, Pasadena, TX (US); Kimberly M. White, Baton Rouge, LA (US); Scott E. Angell, Pasadena, TX (US); Arthur G. Mack, Prairieville, LA (US)

(73) Assignee: Albemarle Corporation, Baton Rouge, LA (US)

( * ) Notice: Subject to any disclaimer, the term of this patent is extended or adjusted under 35 U.S.C. 154(b) by 12 days.

This patent is subject to a terminal disclaimer.

(21) Appl. No.: 14/464,156

(22) Filed: Aug. 20, 2014

(65) Prior Publication Data

US 2014/0357885 A1 Dec. 4, 2014

Related U.S. Application Data

(63) Continuation of application No. 13/319,491, filed as application No. PCT/US2010/035359 on May 19, 2010.

(60) Provisional application No. 61/179,519, filed on May 19, 2009.

(51) Int. Cl.
*C07F 9/6574* (2006.01)
*C08K 5/5313* (2006.01)
*C07F 9/6571* (2006.01)
*C08L 21/00* (2006.01)

(52) U.S. Cl.
CPC ..... *C07F 9/65746* (2013.01); *C07F 9/657172* (2013.01); *C08K 5/5313* (2013.01); *C08L 21/00* (2013.01)

(58) Field of Classification Search
None
See application file for complete search history.

(56) References Cited

U.S. PATENT DOCUMENTS

| | | |
|---|---|---|
| 5,814,704 A | 9/1998 | Andrianov et al. |
| 6,441,067 B1 | 8/2002 | Chiu et al. |
| 7,053,138 B2 | 5/2006 | Magendie et al. |
| 2003/0034482 A1 | 2/2003 | Kinoshita et al. |
| 2005/0038279 A1 | 2/2005 | Dittrich et al. |
| 2006/0102882 A1 | 5/2006 | Bedner et al. |
| 2006/0247344 A1 | 11/2006 | Mueller et al. |
| 2007/0060673 A1 | 3/2007 | Tobisawa et al. |

FOREIGN PATENT DOCUMENTS

| | | |
|---|---|---|
| DE | 102007028593 A1 | 12/2008 |
| JP | 11106619 A | 4/1999 |
| JP | 2001270993 A | 10/2001 |
| JP | 2002193985 A | 7/2002 |
| WO | 2008119693 A1 | 10/2008 |

OTHER PUBLICATIONS

Samperi, F.; Puglisi, C.; Alicata, R.; Montaudo, G. Thermal degradation of poly(ethylene terephthalate) at the processing temperature. Polymer Degradation and Stability, 2004, vol. 83, pp. 3-10.*
NuFR DOPO. Nutech Fine Chemical Co., Ltd. http://www.nu-tech.com.tw/PDF/NuFR%20DOPO.pdf. as viewed on Nov. 10, 2015.*
Wade, Jr., L. G.; Organic Chemistry. Fifth Edition. Pearson Education, Inc. 2003. pp. 759-760.*
XP-008099832; Johannes Artner, et al.; "A Novel and Effective Synthetic Approach to 9, 10-Dihydro-9-oxa-10-phosphaphenanthrene-10-oxide (DOPO) Derivatives"; Phosphorus, Sulfur, and Silicon; 2007; p. 2131-2148; vol. 182; No. 9; Taylor & Francis Group, LLC; US.
XP-002499618; Edward D. Weil; "Flame Retardants, Phosphorus"; Kirk-Othmer Encyclopedia of Chemical Technology; pp. 484-510; vol. 11; Online—Posted Dec. 4, 2000; John Wiley & Sons, Inc.; US.
Abrunhosa-Thomas, I.; Sellers, Claire E.; and Montchamp, J. "Alkylation of H-Phosphinate Esters under Basic Conditions", Journal of Organic Chemistry; 2007, vol. 72, pp. 2851-2856.

* cited by examiner

*Primary Examiner* — Robert C Boyle
*Assistant Examiner* — Stephen Rieth
(74) *Attorney, Agent, or Firm* — James A. Jubinksy; Nathaniel C. Dunn; Marcy M. Hoefling

(57) ABSTRACT

The present invention relates to novel, halogen-free flame retardant derived from 9,10-Dihydro-9-Oxa-10-Phosphaphenantrene-10-oxide (DOPO). This invention also relates to the use of the halogen free DOPO derived flame retardant in polymers.

7 Claims, No Drawings

DOPO DERIVATIVE FLAME RETARDANTS

FIELD OF THE INVENTION

The present invention relates to novel, halogen-free flame retardant derived from 9,10-Dihydro-9-Oxa-10-Phosphaphenantrene-10-oxide (DOPO). This invention also relates to the use of the halogen free DOPO derived flame retardant in polymers.

BACKGROUND OF INVENTION

Polymers as a class of materials are generally flammable. Owing to their combustibility, thermoplastic and thermoset polymers, for example polyamides, polyesters, epoxy resins and polyurethanes, require the use of flame retardants fir many applications. Typically, halogenated compounds, more specifically, aromatic polybrominated compounds, have been used as flame retardant additives in polymers. It is generally accepted that these products inhibit radical gas phase reactions from occurring in the flame when these products are ignited. This makes halogenated flame retardants very commonly used additives for different types of polymeric materials. However, during the last fifteen years or so, halogenated flame retardants have come under scrutiny because of ecological concerns. At this time, the flame retardant industry is under pressure to change to flame retardants that are perceived to be more environmentally friendly, such as organophosphorus flame retardants.

A wide variety of organophosphorus compounds have been shown in the prior art to impart flame retardancy to polymers. Most of the phosphorus-containing flame retardants provide flame retardant activity through a combination of vapor and condensed phase reactions, polymer carbonization promotion, and char formation. However, there are usually problems associated with the use of organophosphorus flame retardant materials. One source of difficulty relates to the processing of polymers, which often requires high temperatures, potentially at temperatures above 210° C. and often as high as 310-350° C. Unfortunately, flame retardants often participate in decomposition or side reactions, which impart undesirable properties to the base polymer or polymer system. Other flame retardants become too volatile under processing conditions and are not effectively retained during processing.

It is desirable therefore, to develop new flame retardants, which are thermally and hydrolytically stable and able to withstand high temperature polymer processing.

SUMMARY OF THE INVENTION

The present invention relates to a compound, useful for a flame retardant, having the following structure:

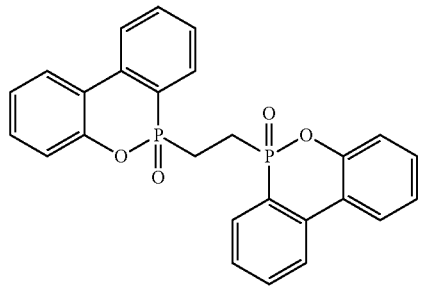 [SMILES: O=P1(CCP2(=O)Oc3ccccc3-c3ccccc32)Oc2ccccc2-c2ccccc21]

Formula I

DETAILED DESCRIPTION OF THE INVENTION

The present invention relates to a compound, useful for a flame retardant additive, having the following structure:

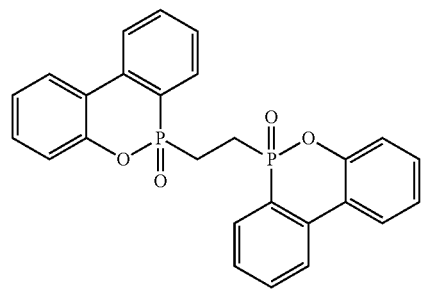

Formula I

This invention also related to a flame retardant polymer composition comprising a polymer and the flame retardant additive of Formula I.

Polymer that may be used in the flame retardant polymer composition include, but are not limited to: polyolefins, polyesters, polyethers, polyketones, polyamides, natural and synthetic rubbers, polyurethanes, polystyrenes, poly(meth) acrylates, phenolic resins, polyacetals, polyacrylonitriles, polybutadienes, polystyrenes, polyimides, polyamideimides, polyetherimides, polyphenylsulfides, polyphenylene oxide, polycarbonates, cellulose, cellulose derivatives, epoxy resins or mixtures thereof. Preferably, the polymers are polyesters, phenolic resins polyamides, polyurethanes, polystyrene, epoxy resins or mixtures thereof.

Another embodiment is when the flame retardant composition further comprises at least one conventional additive, such as heat stabilizers, light stabilizers, ultra-violet light absorbers, anti-oxidants, anti-static agents, preservatives, adhesion promoters, fillers, pigments, dyes, lubricants, mold releasers, blowing agents, fungicides, plasticizers, processing aids, acid scavengers, dyes, pigments, nucleating agents, wetting agents, dispersing agents, synergists, mineral fillers, reinforcing agents such as glass fiber, glass flake, carbon fiber, or metal fiber; whiskers such as potassium titanate, aluminum borate, or calcium silicate; inorganic fillers and other fire-retardant additives, smoke suppressants and mixtures thereof.

The other fire retardant additives which may be used with the compounds of formula I include, but are not limited to, ammonium polyphosphate, nitrogen-containing synergists such as melamine polyphosphate, antimony oxide, silica, hydrated alumina such as aluminum hydroxide (ATH), boehmite, bismuth oxide, molybdenum oxide, or mixtures of these compounds with zinc, aluminum and/or magnesium oxide or salts.

The amount of compound of Formula I added to the polymer as a flame retardant may be varied over a wide range. Usually from about 0.1 to about 100 parts by weight of the compound of Formula I is used per 100 parts by weight of polymer. Preferably about 0.5 to about 70 parts of the compound of Formula I is used per 100 parts by weight of polymer, or from about 2 to about 50 parts by weight per 100 parts by weight of polymer.

Masterbatches of polymer containing the compound of Formula I of this invention, which is blended with additional amounts of substrate polymer, can contain even higher concentrations of the compound of Formula I, e.g., from about 100 to about 1000, or from about 100 to about 500, or from about 100 to about 250 parts by weight of the compound of Formula I per 100 parts by weight of polymer.

Alternatively, the amount of the phosphorus compound of Formula I in the flame retardant polymer composition is selected so the composition will contain about 0.5 wt % to about 10 wt % or about 1.2 wt % to about 7 wt %, or about 1.5 wt % to about 5 wt % phosphorous content, based on the total weight of the composition Particular polymers that may be used in combination with the compound of Formula I are:

A. Polyphenylene oxides and sulfides, and blends of these polymers with polystyrene graft polymers or styrene copolymers such as high impact polystyrene, EPDM copolymers with rubbers, as well as blends of polyphenylene oxide with polyamides and polyesters.

B. Polyurethanes which are derived from polyethers, polyesters or polybutadiene with terminal hydroxyl groups on the one hand and aliphatic or aromatic polyisocyanates on the other hand including polyisocyanurates, as well as precursors thereof.

C. Polyamides manning copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene iso-phthalamide, as well as copolymers thereof with polyethers, such as with polyethylene glycol, polypropylene glycol or polytetramethylene glycols.

D. Polyesters which are derived from dicarboxylic acids and di-alcohols and/or from hydroxycarboxylic acids or the corresponding lactones, such as polyethylene terephthalate, polybutylene terephthalate, poly-1,4-dimethylol-cyclohexane terephthalate and polyhydroxybenzoates as well as block-copolyether-esters derived from polyethers having hydroxyl end groups.

E. Polystyrene and graft copolymers of styrene, for example styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with random copolymers of styrene or α-methylstyrene with dienes or acrylic derivatives, for instance the terpolymers of styrene known as ABS, MBS, ASA or AES terpolymers.

F. Epoxy resins are compounds that are prepared by polyaddition reaction of an epoxy resin component and a cross-linking (hardener) component. The epoxy resin components used are aromatic polyglycidyl ethers such as bisphenol A diglycidyl ether, bisphenol F diglycidyl ether, polyglycidyl ethers of phenol-formaldehyde resins and of cresol-formaldehyde resins, polyglycidyl ethers of phthalic, isophthalic and terephthalic acid, and also of trimellitic acid, N-glycidyl compounds of aromatic amines and of heterocyclic nitrogen bases, and also di- and polyglycidyl compounds of polyhydric aliphatic alcohols. The hardeners used are polyamines such as dicyandiamide (DICY), phenolic novolacs, cresol novolacs, triethylenetetramine, aminoethylpiperazine and isophoronediamine, polyamindoamines, polybasic acids or anhydrides thereof, for example phthalic anhyride, hexahydrophthalic anhydride, methyltetrahydrophthalic anhydride or phenols. The cross-linking may also be affected by polymerization using suitable catalysts or promoters, such as 2-phenylimidazole, 2-methylimidazole, benzyl dimethylamine (BDMA), etc.

G. Polycarbonates.

Polyesters, phenolic resins, polyamides, polyurethanes, polystyrene and epoxy resins are particularly suitable.

The flame retardant additive of Formula I may be incorporated into the polymer by a variety of mixing techniques, such as solution blending and melt blending. Examples of melt blending equipment include twin screw extruders, single screw extruders, Banbury mixers, roll mixers, kneaders, etc. The melt blending temperature depends on the resin being used and is within the range from about 150° C. to about 400° C. When using an extruder for melt blending, in some instances, the extrudate exits through small die holes, and the strands of molten composition are cooled by passing through a water bath. The cooled strands can be pelletized. The pellets can be used to prepare molded articles. In some instances, it is necessary to dry the composition prior to molding. A further technique is to add the flame retardant to finished polymer granules or powders and to process the mixture directly to provide a plastic article.

The method used in producing a plastic article from the flame retardant resin composition of the present invention is not particularly limited, and any method commonly used may be employed. Exemplary such methods include moldings such as injection molding, blow molding, extrusion, sheet forming, thermal molding, rotational molding, and lamination.

The aforementioned flamed retardant may especially be used to form prepreg and/or laminates with epoxy compounds. Typical procedures for forming prepregs and laminates for printed wiring boards involve such operations as:

A) An epoxy-containing formulation such as one containing the aforementioned flame retardant with an epoxy compound is formulated with solvents and curing or polymerization agents and optionally other conventional additives described above. The formulation is applied to or impregnated into a substrate by rolling, dipping, spraying, other known techniques and/or combinations thereof. The substrate is an inorganic or organic reinforcing agent in the form of fibers, fleece, fabric, or textile material, e.g., typically a woven or non-woven fiber mat containing, for instance, glass fibers or paper.

B) The impregnated substrate is "B-staged" by healing at a temperature sufficient to draw off solvent in the epoxy formulation and optionally to partially cure the epoxy formulation, so that the impregnated substrate cooled to room temperature is dry to the touch and can be handled easily. The "B-staging" step is usually carried out at a temperature of from 90° C. to 240° C. and for a tune of from 1 minute to 15 minutes. The impregnated substrate that results from B-staging is called a "prepreg". The temperature is most commonly 100° C. for composites and 130° C. to 200° C. for electrical laminates.

C) One or more sheets of prepreg are stacked or laid up in alternating layers with one or more sheets of a conductive material, such as copper foil, if an electrical laminate is desired.

D) The laid-up sheets are pressed at high temperature and pressure for a time sufficient to cure the resin and form a laminate. The temperature of this lamination step is usually between 100° C. and 240° C., and is most often between 165° C. and 200° C. The lamination step may also be carried out in two or more stages, such as a first stage between 100° C. and 150° C. and a second stage at between 165° C. and 200° C. The pressure is usually between 50 N/cm² and 500 N/cm². The lamination step is usually carried out for a time of from 1 minute to 200 minutes, and most often for 45 minutes to 120 minutes. The lamination step may optionally be carried out at higher temperatures for shorter times (such as in continuous lamination processes) or for longer times at lower temperatures (such as in low energy press processes).

E) Optionally, the resulting laminate, for example, a copper-clad laminate, may be post-treated by heating for a time at high temperature and ambient pressure. The temperature of post-treatment is usually between 120° C. and 250° C. The post-treatment usually is between 30 minutes and 12 hours.

F) Often an electrically-conductive printed circuit is applied to the copper-clad laminate.

Typically, the solvent for the epoxy resin in step A above is a ketone such as 2-butanone or methyl ethyl ketone (MEK). However, any other suitable type of conventionally-used solvent for forming these formulations can be employed. Examples of such other solvents include, but are not limited to acetone, methyl isobutyl ketone (MIBK), 2-methoxy ethanol, 1-methoxy-2-propanol, propylene glycol monomethyl ether, ethylene glycol monoethyl ether acetate, toluene, N,N-dimethylformamide, and mixtures thereof.

The curing or polymerization initializing agents that may be used for preparing the laminates are not limited to a specific curing or polymerization initializing agent as long as the agent helps polymerization of the epoxy resin in the flame retardant epoxy composition.

Examples of polymerization initializing agents are cationic polymerization initializing agents such as methane sulfonic acid, aluminum chloride, stannum chloride, trifluoroboron ethylamine complex, trifluoroboron ethylether complex and the like; radical polymerization initializing agents such as benzoyl peroxide, dicumyl peroxide, azo bis-isobutyronitrile and the like; and anionic polymerization initializing agents such as methoxy potassium, triethyl amine, 2-dimethyl aminophenol and the like and mixtures thereof.

The aforementioned epoxy curing agents include any agent known by a person skilled in the art. Examples, include but are not limited to: ethylene diamine, trimethylene diamine, tetramethylene diamine, hexamethylene diamine, meta phenylene diamine, para phenylene diamine, para xylene diamine, 4,4'-diamino diphenyl methane, 4,4'-diamino diphenyl propane, 4,4'-diamino diphenyl ether, 4,4'-diamino diphenyl sulfone, 4,4'-diamino dicyclohexane, bis (4-aminophenyl) phenyl methane, 1,5-diamino naphthalene, meta xylylene diamine, para xylylene diamine, 1,1-bis (4-aminophenyl) cyclohexane, dicyan diamide, phenol/formaldehyde novolac, cresol/formaldehyde novolac, bis-phenol A novolac, biphenyl-, toluene-, xylene-, or mesitylene-modified phenol/formaldehyde novolac, aminotriazine novolac, cresol/formaldehyde/aminotriazine novolac, phenol/formaldehyde/aminotriazine novolac or mixtures thereof.

The amount of curing agent that may be used is based on the molar equivalence of curing functional groups in the curing agent to the molar equivalence of un-reacted epoxy groups in the phosphorus-containing epoxy resin. Thus, the curing agent amount may be from about 0.1 equivalence to about 10 equivalence or about 0.3 equivalence to about 5 equivalence, or about 0.7 equivalence to about 2 equivalence based on the equivalence of unreacted epoxy groups in the phosphorus-containing epoxy resin.

The polymerization initializing agents may be added in concentrations ranging from about 0.01 wt % to about 10 wt %, or about 0.05 to about 5%, or about 0.1 wt % to about 2 wt %, based on the total weight of the cured epoxy resin.

The curing temperature may be carried out generally between about 25° C. to about 250° C., or about 70° C. to about 240° C. or about 150° C. to about 220° C.

In addition, epoxy curing agent promoters may also be used to promote curing of the epoxy compositions. These epoxy curing agent promoters are often based on imidazoles. Examples of such epoxy curing agent promoters include, but are not limited to: 1-methylimidazole, 2-methylimidazole, 1,2-dimethylimidazole, 1,2,4,5-tetramethylimidazole, 2-ethyl-4-methylimidazole, 2-phenylimidazole 1-cyano-ethyl-2-phenylimidazole, 1-(4,6-diamino-s-triazinyl-2-ethyl)-2-phenylimidazole or mixtures thereof.

When phenol novolacs are used as curing agents, the epoxy curing agent promoter may be added in concentrations ranging, from about 0.0001 wt % to about 5 wt %, or about 0.01 to about 3%, or about 0.1 wt % to about 2 wt %, or about 0.15 wt % to about 1 wt %, based on the weight of curing agent used. Higher concentrations of promoter may be used with different curing agents, such as DICY, dicyandiamide, where promoter concentrations are more typically in the 5-25 wt % range, based on weight of curing agent.

The curing temperature may be carried out generally between about 25° C. to about 250° C., or about 70° C. to about 240° C. or about 150° C. to about 220° C.

Reaction Procedure

The present invention also relates to a process of making a compound having the following structure:

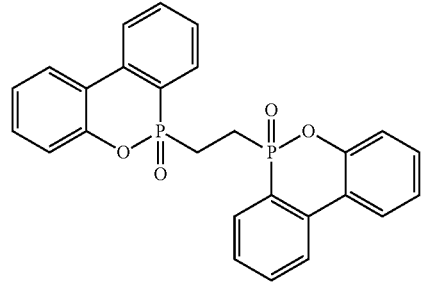

Formula I comprising reacting a compound of Formula A

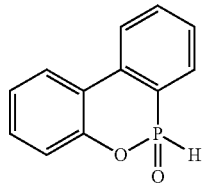

Formula A with dihaloethane, such as dichloroethane or dibromoethane, in the presence of a base.

One base that may be used is an alkali metal base such as alkali metal alkoxides, alkali metal amides and alkali metal alkyl amides. Alkali metals for the base include lithium, sodium and potassium. Examples of the bases that may be used include, but are not limited, to, potassium methoxide, sodium methoxide, lithium methoxide, potassium ethoxide, sodium ethoxide, lithium ethoxide, potassium t-butoxide, sodium t-butoxide, lithium diisopropyl amide and mixtures thereof. Preferred are potassium t-butoxide and sodium methoxide.

Any suitable amount of base may be used in the process of this invention. Such suitable amounts include from about 0.1 to about 10 equivalence, or about 0.5 to about 5 equivalence, based on the amount of the compound of Formula A.

The process may also contain an optional solvent. Examples of such solvents may include, but are not limited to, heptane, hexane, petroleum ether, methylcyclohexane; toluene, xylene, ethyl benzene, tetrahydrofuran, dimethyl sulfoxide (DMSO), 1,4-dioxane, dimethyl formamide (DMF), dimethylacetamide (DMAc), acetonitrile, ethylene glycol dimethyl ether, ethylene glycol diethyl ether or mixtures thereof.

The process may be conducted at temperatures ranging from about −10° C. to about 100° C.

The following Examples illustrate the present invention. It is to be understood, however, that the invention, as fully described herein and as recited in the claims, is not intended to be limited by the details of the following Examples.

Example 1

6H-Dibenz[c,e][1,2]oxaphosphorin, 6,6'-(1,4-ethanediyl)bis-,6,6'-dioxide

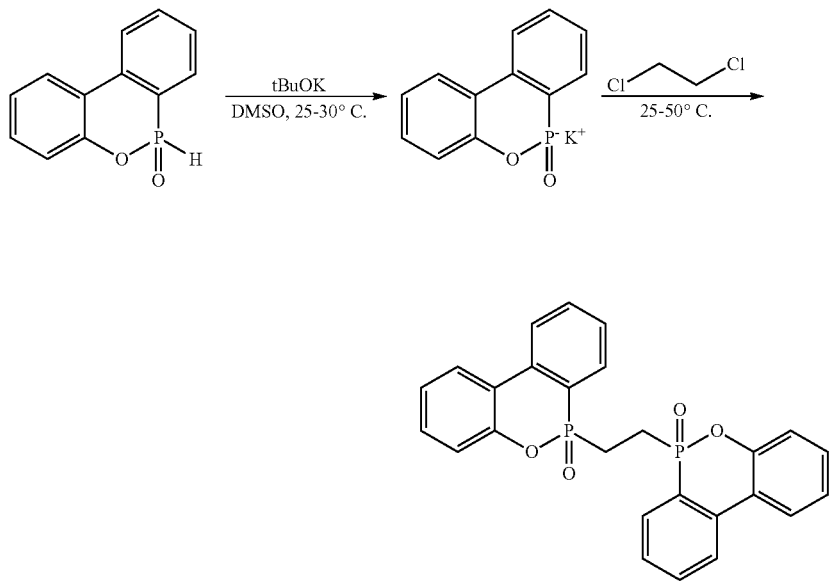

| Component | MW (g/mol) | m.p (° C.) | b.p (° C.) | Physical state | moles | grams | mls | Eq. |
|---|---|---|---|---|---|---|---|---|
| DOPO, CAS # 35948-25-5 TCI America | 216.17 | 119 | — | Solid | 1.96 | 423 | — | 2.1 |
| tBuOK, CAS # 865-47-4, Sigma-Aldrich, St. Louis, MO | 112.21 | 256-258 | — | Solid | 2.05 | 230 | — | 2.2 |
| DMSO, CAS # 67-68-5, Sigma-Aldrich, St. Louis, MO | 78.13 | 16-19 | 189 | Liquid | 21.12 | 1650 | 1500 | 12 |
| Dichloroethane CAS # 75-34-3, Sigma-Aldrich, St. Louis, MO | 98.96 | −35 | 83 | Liquid | 0.93 | 92 | 73 | 1.0 |

A 4-neck 5 L half-jacketed reactor was fitted with an addition funnel, thermocouple, mechanical stirrer and nitrogen flow. The reactor was charged with potassium t-butoxide (tBuOK) (230 g, 2.05 mol) and 1.5 L of anhydrous DMSO as solvent. The mixture was stirred at room temperature until it became a homogenous solution. The solution was cooled to 10° C. and DOPO (423 g, 1.96 mol) was added in nine small portions, keeping the reaction temperature below 30° C. (50-60 g per portion). Dichloroethane (92 g, 0.93 mol) in a 125 ml addition funnel was added to the above solution slowly during 1 h. The reaction was heated to 50° C. for 1 h. The reaction was cooled to 10° C., and water (3 L) was added. The slurry was filtered, and the wet cake was washed with water, acetone and ethyl acetate to give 32 g of crude wet material. The crude material was refluxed in MeCN/ethanol/$H_2O$ (5320 ml, v:v:v=1:1:0.5) and cooled to 5° C. slowly. The white solid was filtered through a coarse fitted funnel and dried in a vacuum oven for 8 h at 80° C. to afford a dry white powder (260 g, 68 wt % yield, 99.4 wt % purity, 253-269° C. m.p.). $^{31}$P-NMR (162 MHz, $CDCl_3$): δ36.45, 36.25 ppm and $^1$H-NMR (400 MHz, $CDCl_3$): δ7.95 (d, J=8 Hz, 2H, ArH), 7.88 (d, J=8 Hz, 2H, ArH), 7.79-7.69 (m, 4H, ArH), 7.48 (dd, J=7.2 Hz, 14.4 Hz, 2H), 7.37 (dd, J=7.2 Hz, 7.2 Hz, 2H, ArH), 7.29-7.24 (m, 2H, ArH), 7.16 (d, J=12 Hz, 2H, ArH), 2.31 (m, 4H) ppm.

Example 2

Use of 6H-Dibenz[c,e][1,2]oxaphosphorin, 6,6'-(1, 4-ethanediyl)bis-,6,6'-dioxide in epoxy laminate (4% phosphorus content)

In general, stock solutions of advanced resin, curative and promoter are all prepared and stored separately to facilitate experimentation. An 85 wt % phenol epoxy novolac resin solution, DEN® 438-EK85, containing 15 wt % 2-butanone (MEK) was obtained from The Dow Chemical Company, Durite SD-1702 novolac curing agent was obtained from Hexion Corporation. A novolac resin solution was prepared by dissolving 50 wt % SD-1702 in 50 wt % MEK solvent.

The flame retardant of Example 1 (6H-Dibenz[c,e][1,2] oxaphosphorin, 6,6'-(1,4-ethanediyl)bis-,6,6'-dioxide) containing 13.5 wt % P was ground using a coffee bean grinder. A flame retardant resin mixture containing 4.0 wt % P was prepared by blending 6.31 g of 85 wt % DEN 438 solution, 6.30 g of 50 wt % SD-1702 solution, 3.59 g flame retardant, 0.006 g 2-phenylimidazole promoter (approximately 1.1 mL of a solution containing 0.277 g 2-PhI in 50 mL MEK). The novolac to promoter ratio was about 525. The flame retardant was insoluble in the resin solution until making contact with the hot gel plate, where it dissolved completely at high temperature. About 0.5-1 mL of the resin mixture was added to a hot cure plate (Thermo-electric company) at about 162-164° C. A tongue depressor was split in half lengthwise, and half of the depressor was used to move the resin on the hot plate until stiffness was noted and then lifting the resin with the at part of the depressor until string formation ceased. The gel time was 4 minutes, 43 seconds, determined by the point where resin "strings" could no longer be pulled from the resin mixture and the epoxy became "tack free".

A larger flame retardant resin varnish containing 4.0 wt % P was prepared in an 8 oz wide-mouth glass jar by adding 63.14 g of 85 wt % DEN 438 solution, 63.00 g of 50 wt % SD-1702 solution, 35.92 g flame retardant and 0.060 g 2-phenylimidazole promoter. An additional 30 g MEK was added to the resin solution. The resin mixture was mixed thoroughly using a high shear mixer stirred at 6,000 rpm for about 15 minutes.

An 11 inch by 11 inch square woven glass fabric (7628 glass with 643 finish from BGF Industries) was cut to size from a large roll and stapled to wood supports (12 inches long, 1 inch wide and 1/16 inch thick) on the top and bottom ends of the fabric. The wood supports contained holes in the cornets for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for 3 minutes, 50 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (1/8 inch thick, 12 inch by 12 inch square dimensions). The laminate was formed in the hot press at 5,000 psig for 1 hour. The resulting laminate was 0.034 inches thick, contained 45 wt % resin and underwent 13 wt % resin overflow during pressing. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting in a V-0 rating with 32 seconds total burn time for the two ignitions on all five coupons.

Example 3

Use of 6H-Dibenz[c,e][1,2]oxaphosphorin, 6,6'-(1, 4-ethanediyl)bis-,6,6'-dioxide in epoxy laminate (3% phosphorus content)

In general, stock solutions of advanced resin, curative and promoter are all prepared and stored separately to facilitate experimentation. An 85 wt % phenol epoxy novolac resin solution, DEN® 438-EK85, containing 15 wt % 2-butanone (MEK) was obtained from The Dow Chemical Company. Durite SD-1702 novolac curing agent was obtained from Hexion Corporation. A novolac resin solution was prepared by dissolving 50 wt % SD-1702 in 50 wt % MEK solvent.

The flame retardant of Example 1 (6H-Dibenz[c,e][1,2] oxaphosphorin, 6,6'-(1,4-ethanediyl)bis-,6,6'-dioxide) containing 13.5 wt % P was ground using a coffee bean grinder. A flame retardant resin mixture containing 3.0 wt % P was prepared by blending 126.3 g of 85 wt % DEN 438 solution, 126.0 g of 50 wt % SD-1702 solution, 48.8 g flame retardant, 0.12 g 2-phenylimidazole promoter. The novolac to promoter ratio was about 525. The flame retardant was insoluble in the resin solution until making contact with the hot gel plate, were it dissolved completely at high temperature. About 0.5-1 mL of the resin mixture was added to a hot cure plate (Thermo-electric company) at about 162-164° C. A tongue depressor was split in half lengthwise, and half of the depressor was used to move the resin on the hot plate until stiffness was noted and then lifting the resin with the flat part of the depressor until string formation ceased. The gel time was 4 minutes, 22 seconds, determined by the point where resin "strings" could no longer be pulled from the resin mixture and the epoxy became "tack free". An additional 70 g MEK was added to the resin solution. The resin mixture was mixed thoroughly using a high shear mixer stirred at 6,000 rpm for about 15 minutes.

An 11 inch by 11 inch square woven glass fabric (7628 glass with 643 finish from BGF industries) was cut to size from a large roll and stapled to wood supports (1.2 inches long, 1 inch wide and 1/16 inch thick) on the top and bottom ends of the fabric. The wood supports contained holes in the corners for inserting paper clips on one cod for hanging the fabric, in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip dry for about one minute before hanging in a pre-heated (to 170° C.) forced air Blue M oven (Lab Safety Supply Inc., a unit of General Signal) for 3 minutes, 30 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (1/8 inch thick, 12 inch by 12 inch square dimensions). The laminate was formed in the hot press at 5,000 psig for 1 hour. The resulting laminate was 0.037 inches thick, contained 49 wt % resin and underwent 3 wt % resin overflow during pressing. Five 0.5 inch wide coupons were cut from the laminate using a diamond saw, and the coupon edges were smoothed with sandpaper. The flammability of the coupons were screened by ASTM D3801-06 using an Atlas UL-94 burn chamber, resulting, in a V-1 rating with 56 seconds total burn time for the two ignitions on all five coupons. No single burn was greater than 10 seconds.

Comparison Example 4

Laminate Preparation from DEN 438 Novolac Epoxy Resin with No Flare Retardant

In general, stock solutions of advanced resin, curative and promoter are all prepared and stored separately to facilitate experimentation. An 85 wt %, phenol epoxy novolac resin solution, DEN® 438-EK85, containing 15 wt % 2-butanone (MEK) was obtained from The Dow Chemical Company, Durite SD-1702 novolac curing agent was obtained from Hexion Corporation. A novolac resin solution was prepared by dissolving 50 wt % 5.0-1702 in 50 wt % MEK solvent.

A resin mixture containing no flame retardant was prepared by blending 113.64 g of 85 wt % DEN 438 solution, 113.40 g of 50 wt % SD-1702 solution and 0.0705 g 2-phenylimidazole promoter into a 400 mL disposable plastic beaker. The novolac to promoter ratio was about 804. About 0.5-1 mL of the resin solution was added to a hot cure plate (Thermo-electric company) at about 162-164° C. A tongue depressor was split in half lengthwise, and half of the depressor was used to move the resin on the hot plate until stiffness was noted and then lifting the resin with the flat part of the depressor until string formation ceased. The gel time was 5 minutes, 30 seconds, determined by the point where resin "strings" could no longer be pulled from the resin mixture and the epoxy became "tack free".

A 12 inch by 12 inch square woven glass fabric (JPS 7628 Fiber Glass Cloth having a CS-718 finish) was cut to size from a large roll and stapled to wood supports (12 inches long, 1 inch wide and 1/16 inch thick) on the top and bottom ends of the fabric. The wood supports contained holes in the corners for inserting paper clips on one end for hanging the fabric in the B-stage oven. The A-stage, or resin varnish, was painted on the front and back of the fabric. Paper clips were unfolded and inserted into the both holes of one wood support. The resin-saturated fabric was hung from aluminum supports in a laboratory fume hood and allowed to drip thy for about one minute before hanging in a pre-heated (to 170° C.) forced air Blue M oven (Lab Safety Supply Inc, a unit of General Signal) for a period of time between 4 minutes, 10 seconds and 4 minutes, 30 seconds. The edges of the B-staged prepreg were removed by reducing the sheet dimensions to 10 inch by 10 inch. The sheet was cut into four 5 inch by 5 inch sheets and weighed before stacking the four layers of prepreg between two layers of Pacothane release film (Insulectro Corp.) and two steel plates (1/8 inch thick, 12 inch by 12 inch square dimensions). The laminate was formed in the hot press at 5,000 psig for 1 hour. The resulting laminates were between 0.034 inches and 0.036 inches thick, contained between 44 wt % and 46 wt % resin and underwent between 1 wt % and 18 wt % resin overflow during pressing. Five (1.5 inch wide coupons were cut from the laminate using, a diamond saw, and the coupon edges were smoothed with sandpaper. The flammability of the coupons was screened by ASTM D3801-06 using an Atlas UL-94 burn chamber, resulting in burn ratings on all sets of five coupons.

Characterization of Laminates

Flame retardant and thermal properties of the laminate of Example 2 with 4 wt % phosphorus content and the laminate of Example 3 with 3 wt % phosphorus content were compared to Comparison Example 4 as shown below in Table 1. The flammability (UL-94 ratings) of the laminates was screened by ASTM D3801-06 using an Atlas UL-94 burn chamber (V-O being highest possible rating). The thermogravimetric analysis (TGA) and glass transition temperature (Tg) rate rise was 10° C./min in $N_2$.

TABLE 1

CHARACTERIZATION OF LAMINATES

|  | Inventive Example 2 | Inventive Example 3 | Comparison Example 4 (No Flame retardant) |
|---|---|---|---|
| UL-94 | V-0 | V-1 | Burn |
| Phosphorus content | 4.0% | 3.0% | 0% |
| Tg (Glass transition temperature | 126-131° C. | 136-140° C. | 163-172° C. |
| TGA 5%-wt Loss | 405-411° C. | 405-411° C. | 407-421° C. |

Components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what chemical changes, transformations and/or reactions, if any, take place in the resulting mixture or solution as such changes, transformations, and or reactions are the natural result of bringing the spilled components together under the conditions called for pursuant to this disclosure. Thus the components are identified as ingredients to be brought together in connection with performing a desired operation or in forming a desired composition. Also, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and or ingredients in accordance with the present disclosure. The fact that a

What is claimed is:

1. A compound having the following structure:

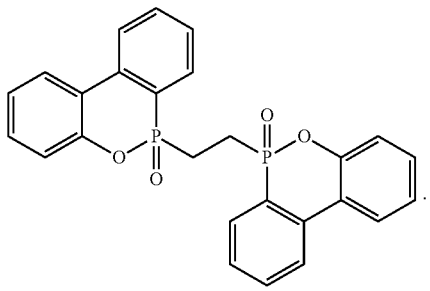 [SMILES: O=P1(CCP2(=O)Oc3ccccc3-c3ccccc32)Oc2ccccc2-c2ccccc21]

2. A composition comprising the compound of claim 1, wherein said composition has an unreacted DOPO concentration of less than about 50,000 ppm.

3. A composition comprising the compound of claim 1, wherein said composition has a solvent concentration less than about 1,000 ppm.

4. A composition comprising the compound of claim 1, wherein the amount of said compound in the composition is greater than about 95 wt %.

5. A composition comprising the compound of claim 1, wherein said composition has a 5% TGA weight loss at a temperature of greater than about 245° C.

6. A composition comprising the compound of claim 1, wherein said composition has a total chlorine or bromine concentration less than about 1000 ppm.

7. A process for preparing the compound of Formula I:

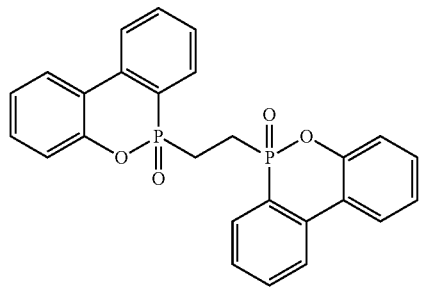

Formula I comprising reacting a compound of Formula A

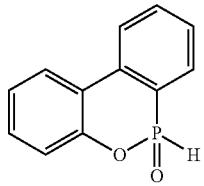

Formula A with dihaloethane in the presence of a base said base is potassium methoxide, sodium methoxide, lithium methoxide, potassium ethoxide, sodium ethoxide, lithium ethoxide, potassium t-butoxide, sodium t-butoxide, or mixtures thereof.

* * * * *